United States Patent
Miyajima (10) Patent No.: US 9,168,019 B2
(45) Date of Patent: Oct. 27, 2015

(54) ULTRASONIC DIAGNOSTIC DEVICE

(75) Inventor: Yasuo Miyajima, Utsunomiya (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 304 days.

(21) Appl. No.: 13/128,885

(22) PCT Filed: Jun. 23, 2010

(86) PCT No.: PCT/JP2010/004180
§ 371 (c)(1),
(2), (4) Date: May 12, 2011

(87) PCT Pub. No.: WO2010/150539
PCT Pub. Date: Dec. 29, 2010

(65) Prior Publication Data
US 2011/0230767 A1    Sep. 22, 2011

(30) Foreign Application Priority Data

Jun. 24, 2009  (JP) ................. 2009-149931

(51) Int. Cl.
*A61B 5/02* (2006.01)
*A61B 8/00* (2006.01)
*A61B 8/06* (2006.01)

(52) U.S. Cl.
CPC ... *A61B 8/00* (2013.01); *A61B 8/44* (2013.01); *A61B 8/4444* (2013.01); *A61B 8/546* (2013.01); *A61B 8/06* (2013.01)

(58) Field of Classification Search
USPC .......................... 600/407, 437, 459; 382/128
See application file for complete search history.

(56) References Cited

U.S. PATENT DOCUMENTS

| | | | | |
|---|---|---|---|---|
| 5,560,362 A | * | 10/1996 | Sliwa et al. | 600/439 |
| 6,542,846 B1 | * | 4/2003 | Miller et al. | 702/132 |
| 2004/0267137 A1 | * | 12/2004 | Peszynski et al. | 600/459 |
| 2005/0215892 A1 | * | 9/2005 | Emery et al. | 600/437 |
| 2006/0100513 A1 | * | 5/2006 | Hashimoto | 600/437 |

(Continued)

FOREIGN PATENT DOCUMENTS

| | | |
|---|---|---|
| JP | 8 56942 | 3/1996 |
| JP | 3325712 | 7/2002 |

(Continued)

OTHER PUBLICATIONS

International Preliminary Report on Patentability and Written Opinion issued Jan. 17, 2012 in PCT /JP2010/004180.
International Search Report Issued Aug. 31, 2010 in PCT/JP10/004180 filed Jun. 23, 2010.

*Primary Examiner* — Joel F Brutus
(74) *Attorney, Agent, or Firm* — Oblon, McClelland, Maier & Neustadt, L.L.P.

(57) ABSTRACT

An ultrasonic diagnostic device is characterized by being provided with a cooling mechanism for cooling an ultrasonic vibrator by circulating a refrigerant in a cable of an ultrasonic probe in which the ultrasonic vibrator is provided, a cooling abnormality detecting means for detecting the abnormal state of the cooling mechanism, and an operating means for, when the abnormal state of the cooling mechanism is detected by the cooling abnormality detecting means, performing a degraded operation in which the transmission/reception condition of the ultrasonic vibrator is changed according to the detected abnormal state.

7 Claims, 7 Drawing Sheets

(56) References Cited

U.S. PATENT DOCUMENTS

2006/0191344 A1* 8/2006 Hashimoto .................... 73/632
2008/0064955 A1 3/2008 Miyajima

FOREIGN PATENT DOCUMENTS

| | | |
|---|---|---|
| JP | 2006 158411 | 6/2006 |
| JP | 2008 61938 | 3/2008 |

* cited by examiner

| | | |
|---|---|---|
| LOW-POWER MODE | 1 | DECREASE IN TRANSMISSION VOLTAGE |
| | 2 | DECREASE IN BIAS CURRENT IN RECEIVING CIRCUIT |
| | 3 | DECREASE IN TRANSMISSION BEAM WIDTH |
| | 4 | INCREASE IN SCANNING INTERVAL INTERMITTENT SCANNING |
| | 5 | INHIBITION OF SELECTING OPERATION PARAMETER IN WHICH POWER CONSUMPTION IS LARGE |
| | 6 | DECREASE IN NUMBER OF OPERATING ELEMENTS OF ULTRASONIC TRANSDUCER |
| | 7 | OPTIONAL COMBINATION OF ABOVE TIME LIMITING MODE |
| TIME LIMITING MODE | 1 | STOP OF FAN |
| | 2 | DECREASE IN ROTATIONAL NUMBER OF FAN |
| | 3 | STOP OF PUMP |
| | 4 | DECREASE IN ROTATIONAL NUMBER OF PUMP |
| | 5 | REFRIGERANT LEAKAGE (CIRCULATION STOP) |
| | 6 | DECREASE IN REFRIGERANT CIRCULATION |
| | 7 | COMBINATION OF FAILED PORTION AND SITUATION | ered

ULTRASONIC DIAGNOSTIC DEVICE

TECHNICAL FIELD

Embodiments of the invention relate to an ultrasonic diagnostic device.

RELATED APPLICATION

This application is based on the benefit of the priority of the Japanese Patent Application No. 2009-149931 filed on Jun. 24, 2009. The contents of the Japanese application are cited herein to be incorporated to this application.

BACKGROUND ART

In the ultrasonic diagnostic device and the like capable of scanning a three-dimensional image, a device capable of driving ultrasonic transducers in a two-dimensional array by arranging an electronic circuit in an ultrasonic probe unit and performing beamforming to a portion, which is wanted to be observed, is turned into actual use. Heat radiation of such ultrasonic probe unit with high function, high output and high density mounting is an important technical problem. Since sufficient cooling cannot be performed by spontaneous cooling from a surface of a casing of the ultrasonic probe unit, a situation in which an output of an ultrasonic wave is forcedly limited occurs.

Forced cooling to allow a refrigerant to circulate through a probe cable is studied for resolving the problem in cooling. However, in the cable using a soft and flexible tube and the like, leakage of the refrigerant and failure of a pump for circulation often occur, and in such a case, cooling performance is deteriorated and there is a possibility that a surface temperature of the ultrasonic probe unit cannot be maintained within a safe range. In accordance with the regulations that the surface temperature of the ultrasonic probe unit applied to a patient cannot be higher than a certain temperature in order to prevent low temperature burn, temperature management of the ultrasonic probe unit should be certainly executed in order to prevent medical accident.

Therefore, there is the device in which a temperature sensor is embedded in the ultrasonic probe unit for detecting the temperature by the temperature sensor, thereby adjusting driving power of the ultrasonic transducer such that the temperature of the ultrasonic transducer does not become a reference temperature or higher.

CITATION LIST

Patent Literature

PLT 1: Japanese Patent No. 3325712

SUMMARY OF THE INVENTION

Technical Problem

Although it is necessary to correctly detect the temperature, by control to detect only the temperature, it is not possible to comprehend which portion of the ultrasonic probe unit is failed, so that detailed control operation is extremely difficult. Since the temperature control generally generates time lag, it is possible that the temperature is out of control and overshoots to be higher than the reference temperature (for example, 40° C.), and it is dangerous.

There is a case in which the device cannot be used even though diagnosis is wanted such as in a case in which the device is carried to an accident location by urgent request and in a situation in which an alternative device cannot be waited such as a probe in a body cavity.

The invention provides the ultrasonic diagnostic device capable of being continuously used by the operation in which a part of the operation is stopped (fallback operation) in a case where there is no alternative device in the vicinity.

Solution to Problem

An embodiment provides an ultrasonic diagnostic device including: a cooling mechanism for cooling an ultrasonic probe unit by circulating a refrigerant in a cable of the ultrasonic probe unit in which ultrasonic transducers are provided; cooling abnormality detecting unit configured to detect an abnormal state in the cooling mechanism; and operating unit configured to, when the abnormal state of the cooling mechanism is detected by the cooling abnormality detecting unit, perform fallback operation to change a transmission reception condition of the ultrasonic transducer in accordance with the detected abnormal state.

Advantageous Effects of Invention

According to the ultrasonic diagnostic device of the embodiment, the ultrasonic diagnostic device capable of being continuously used by the operation in which a part of the operation is stopped (fallback operation) in a case where there is no alternative device in the vicinity is obtained.

DESCRIPTION OF EMBODIMENTS

An embodiment is described in detail with reference to the drawings.

Figure 1:
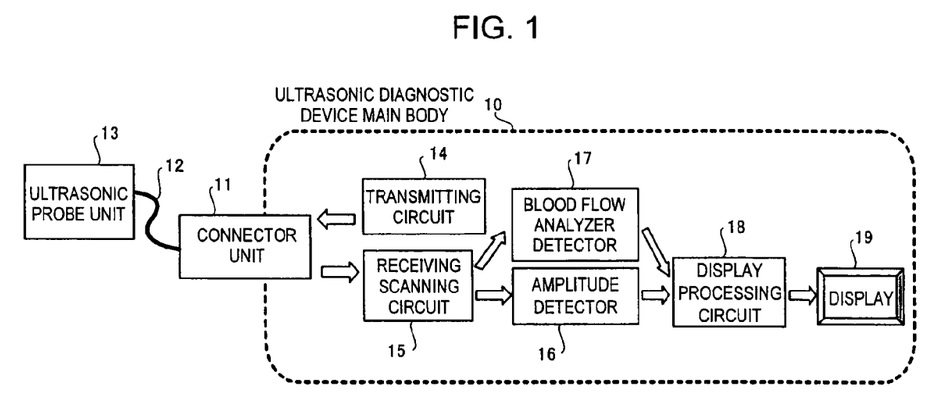
FIG. 1 is a basic configuration diagram of an ultrasonic diagnostic device according to one embodiment.

FIG. 1 is a basic configuration diagram of an ultrasonic diagnostic device according to one embodiment. An ultrasonic diagnostic device main body 10 is used with an ultrasonic probe unit 13 connected to a probe cable 12 connected by a connecter unit 11.

The ultrasonic diagnostic device main body 10 is constituted by a transmitting circuit 14 for generating an ultrasonic wave from the ultrasonic probe unit 13, a receiving scanning circuit 15 for receiving an ultrasonic signal reflected back from inside a subject, an amplitude detecting circuit 16 for generating a tissue morphological image corresponding to a scan mode, a blood flow analyzer detector 17 for generating a blood flow Doppler image, a display processing circuit 18 for synthesizing the tissue morphological image and the blood flow Doppler image, and a display 19 for displaying the synthetic image.

The ultrasonic probe unit 13 is provided in an ultrasonic probe, and an array transducer (not illustrated) in which a plurality of transducers for converting an electric signal and an acoustic signal to each other are arrayed is adopted such that the inside of the subject may be electronically scanned at a high speed by the ultrasonic wave. This is connected to the ultrasonic device main body 10 by the connecter unit 11 through the probe cable 12 for circulating a refrigerant.

The transmitting circuit 14 is constituted by a clock generator, a divider, a transmitting delay circuit and a pulser, which are not illustrated. By dividing a clock pulse generated by the clock generator into a rate pulse of approximately 5 KHz, for example, by the divider, passing the rate pulse through the transmitting delay circuit, and thereafter applying the same to the pulser, a high-frequency voltage pulse is generated to drive an ultrasonic transducer. The ultrasonic transducer mechanically vibrates by this to generate the ultrasonic wave.

The ultrasonic wave thus generated reflects on a boundary of acoustic impedance inside the subject and returns to the ultrasonic probe unit 13 to mechanically vibrate the ultrasonic transducer. In accordance with this, the electric signal is individually generated in each transducer. The electric signal is amplified and is phased/added by the receiving scanning circuit 15. In accordance with this, the directivity of received signal (echo signal) is generated.

The amplitude detector 16 generates B mode image data for providing morphologic information of a tissue based on the echo signal from the receiving scanning circuit 15. The display processing circuit 18 displays the above-described B mode image data generated by the amplitude detector 16 as a cross-sectional image of the tissue morphological image.

The blood flow analyzer detector 17 is a unit for realizing so-called color Doppler imaging (CDI) and is configured to first detect the echo signal from the receiving scanning circuit 15 in quadrature phase to take out a Doppler signal subjected to frequency shift, pass only a specific frequency component of the taken Doppler signal using a moving target indicator (MTI) filter, obtain a frequency of the passed signal by an autocorrelator, and perform arithmetic operation of an average speed, dispersion and power from the frequency by an arithmetic unit.

Meanwhile, it is possible to switch a general Doppler mode for mainly imaging a blood flow (image data by this mode is referred to as blood flow Doppler image data) and a tissue Doppler mode for mainly imaging an internal organ such as a heart muscle (image data by this mode is referred to as tissue Doppler image data) by adjusting a passband of the MTI filter.

Also, the display processing circuit 18 may synthesize to display the blood flow Doppler image data and the tissue morphological image data generated by the above-described blood flow analyzer detector 17. A synthesized image of the tissue morphological image data and the blood flow image data is displayed on the display 19.

Figure 2:
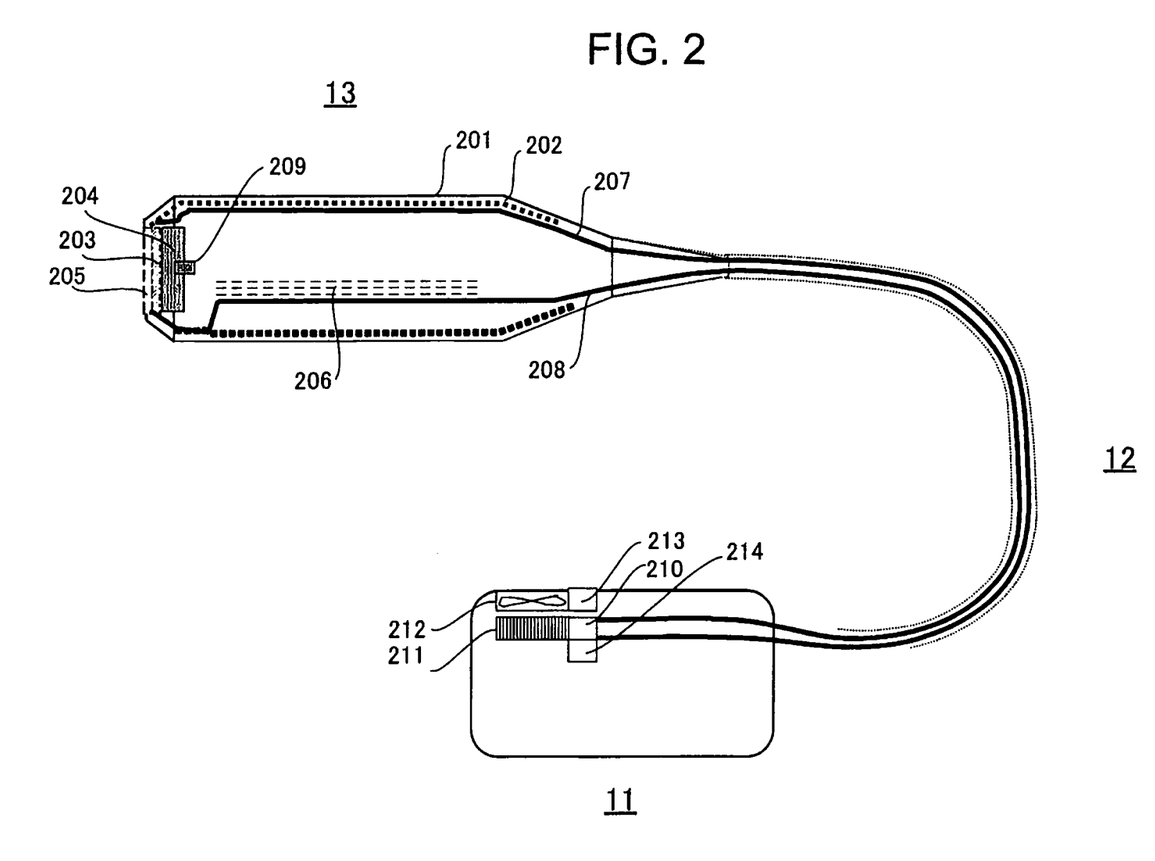
FIG. 2 is a configuration example of a probe of the ultrasonic diagnostic device according to a first embodiment.

FIG. 2 is a configuration example of the probe of the ultrasonic diagnostic device according to a first embodiment. FIG. 2 illustrates a detailed internal configuration of the ultrasonic probe unit 13, the probe cable 12 and the connector 11 illustrated in FIG. 1. A configuration of the ultrasonic probe unit of this embodiment is described with reference to the drawing.

The ultrasonic probe unit 13 is covered with a probe unit exterior 201 and is constituted by a shielding material 202 (indicated by a dotted line) for shielding so as not to emit unnecessary electromagnetic wave to outside, ultrasonic transducers 203 for transmitting and receiving the ultrasonic wave by electric acoustic conversion, a backing material 204 for efficiently emitting the generated ultrasonic wave and receiving the wave, a lens material 205 for serving as an acoustic lens and improving a contacting property with a living body of the subject, an electronic circuit board 206 for performing a process such as generation of an electric acoustic conversion electric signal and amplification of a received electric signal, and a cooling mechanism in which the refrigerant for cooling the ultrasonic transducer 203 circulates. The cooling mechanism is divided into a low-temperature cooling system 207 sent from a pump for cooling the ultrasonic probe unit 13 and the electronic circuit board 206, which generate heat, and a high-temperature cooling system 208 for absorbing the heat of a portion in which the heat is generated and flowing back to the pump. Further, a temperature detecting unit 209 is arranged for detecting a temperature of the ultrasonic transducer 203.

Transmission of the ultrasonic wave by the ultrasonic probe unit 13 applies an electric pulse to the transducer, thereby generating mechanical vibration. Since energy loss is generated at the time of electromechanical conversion, the heat is generated from the ultrasonic transducer 203. The generated vibration is transmitted to the lens material 205 and the backing material 204 and acoustic energy transmitted to the backing material 204 is converted to the heat by damping. The acoustic energy transmitted to the lens material 205 is transmitted into the body of the subject through the lens material 205. There is the attenuation in the lens material 205 and a part of the acoustic energy becomes heat energy.

The shielding material 202 arranged directly below the probe unit exterior 201 has an effect to not only shield an emitted electric wave but also transmit the heat generated from the ultrasonic transducer 203, the lens material 205 and the backing material 204 accompanying with emission of the ultrasonic wave.

The portion in which the heat is generated is mainly the ultrasonic transducer 203 and the electronic circuit board 206. The low-temperature cooling system 207 performs circulation to supply the refrigerant of which temperature is low to first cool the shielding material 202, thereby reducing increase in temperature of a surface of the ultrasonic transducer 203, and thereafter return the refrigerant of which temperature is increased by cooling the electronic circuit board 206 to the high-temperature cooling system 208.

The probe cable 12 is connected to a posterior part of the ultrasonic probe unit 13 and is further connected to the ultrasonic device main body 10 by the connector unit 11. In the cable, coax and wires for control signals and the electric signals including a power supply line and a circulation system of the refrigerant for cooling, that is to say, the low-temperature cooling system 207 and the high-temperature cooling system 208 are included. The probe cable 12 is desirably flexible for improving operability.

The connector unit 11 is constituted by a pump 210 for sending the refrigerant for cooling to the low-temperature cooling system 207 through the probe cable 12, a heat radiator 211 for cooling the refrigerant of the high-temperature cooling system 208, which returns from the cable, and a fan 212 for blowing air to the heat radiator 211.

Further, rotation monitoring unit 213 of the fan 212 for detecting the failure of the cooling system such as the failure of the fan 212, and cooling circulation monitoring unit 214 for detecting abnormal operation of the pump 210 and leakage of the refrigerant are provided. The rotation monitoring of the fan 212 may be easily realized by a circuit and the like for monitoring a power supply current of the fan. Also, abnormality may be detected by a circuit for monitoring the current of the pump for the failure of the pump 210 and by a circuit for monitoring a pressure of the low-temperature cooling system 207 or the high-temperature cooling system 208 for the leakage of the refrigerant.

A surface of the lens material 205 of the ultrasonic probe unit 13 is brought into contact with a body surface of the subject at the time of examination, so that increase in temperature of the surface is a safety problem and it is important to reduce the increase in the temperature of the surface of the lens material 205. The shielding material 202 is connected to the ultrasonic transducer 203 for diffusing the heat generated in the vicinity of the backing material 204 and the ultrasonic transducer 203 and as measures of the emitted electric wave.

A temperature detecting unit 209 is embedded in the backing material 204 for monitoring the surface temperature of the ultrasonic transducer 203 to detect abnormal increase in the temperature. A signal of the temperature detecting unit 209 passes through the probe cable 12 to be transmitted to the ultrasonic diagnostic device main body 10 and the temperature is measured.

The refrigerant of which temperature is decreased by the heat radiator 211 of the connector unit 11 is sent to the low-temperature cooling system 207, which passes through the probe cable 12, by the pump 210, to cool the shielding material 202. The refrigerant of which temperature is increased a little by the shielding material 202 and the ultrasonic transducer 203 is further sent to the electronic circuit board 206 to cool the board and a mounted device, and returned to the heat radiator 211 of the connector unit 11 through the high-temperature cooling system 208 to be cooled.

The heat radiator 211 is cooled by air at a sufficient amount of room temperature of a sufficient amount from the fan 212. When the cooling system normally operates, the ultrasonic transducer 203 and the electronic circuit board 206 are sufficiently cooled and may exert optimal performance using sufficient ultrasonic energy transmission and an optimal received bias current while maintaining the surface temperature of the lens material 205 of the probe unit within a safe range.

Figure 3:
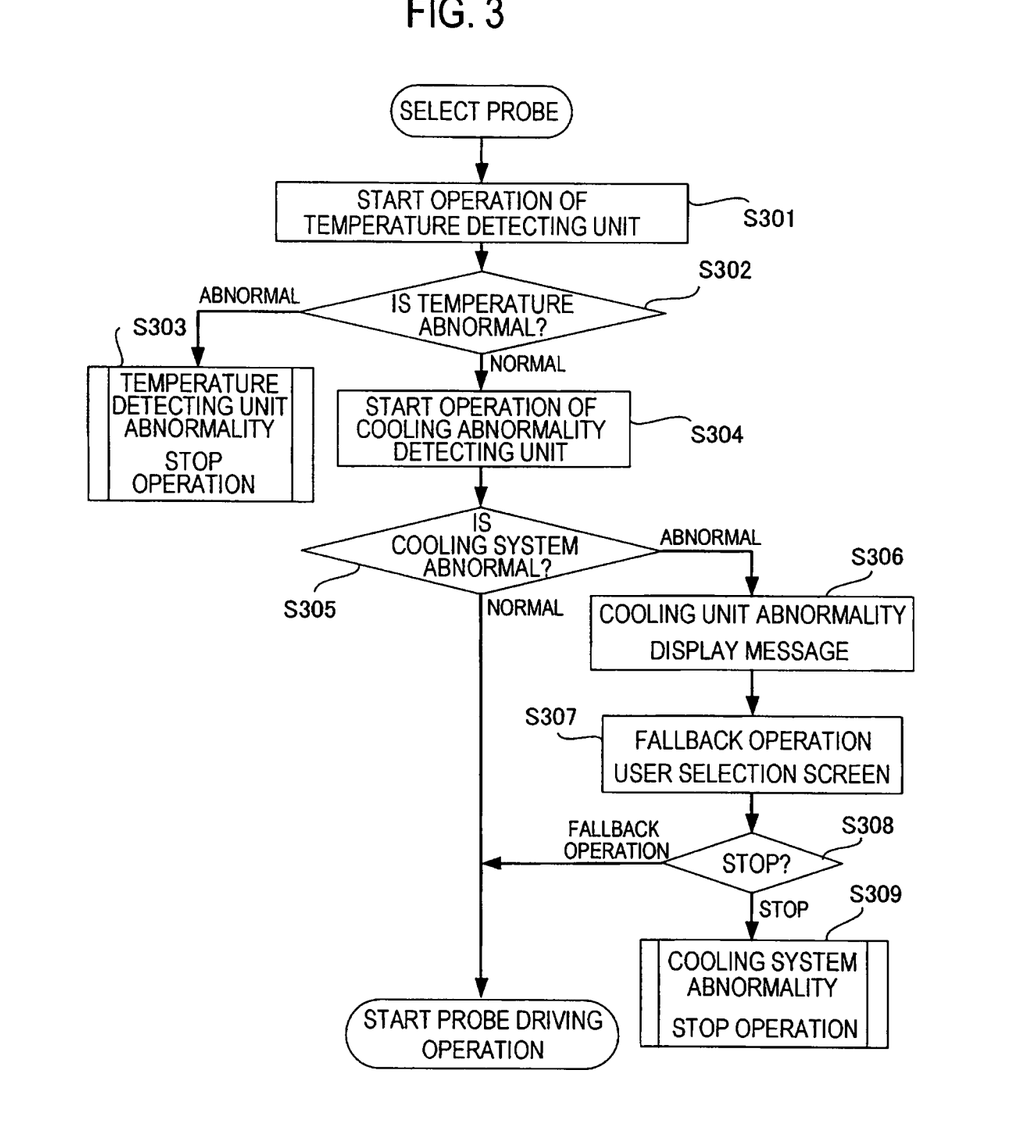
FIG. 3 is a flowchart of initial operation of the ultrasonic diagnostic device according to the first embodiment.
Figure 4:
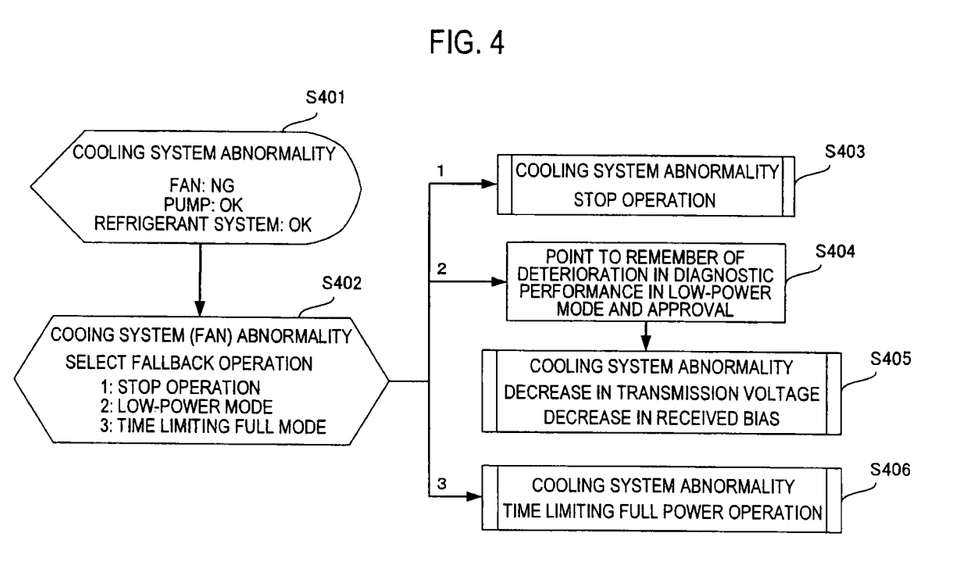
FIG. 4 is a flowchart of a menu and operation of fallback operation of the ultrasonic diagnostic device according to the first embodiment.

FIG. 3 is a flowchart illustrating initial operation of the ultrasonic diagnostic device according to the first embodiment. Also, FIG. 4 is a flowchart illustrating a menu and operation of fallback operation according to the first embodiment. By the flowchart, it is possible to check whether the ultrasonic probe unit 13 to be used may perform the fallback operation characteristic in this embodiment before starting to measure.

The fallback operation herein means operation under a limited condition without completely stopping when the failure occurs in the ultrasonic probe unit 13. In the fallback operation, there are two main types. One is a low-power mode in which diagnostic performance is sacrificed but long time usage is possible and the second one is a time limiting mode in which the diagnostic performance is not deteriorated but operating time is limited in accordance with a failed portion of the cooling system and full power operation is performed.

The low-power mode is the mode to be used while power consumption is inhibited and a transmission reception condition of the ultrasonic transducer 203 is mainly changed. By decreasing a transmission voltage, heat generation of the circuit may be decreased. For example, when the transmission voltage is decreased by 30%, the consumed power may be made substantially half. Decrease in the received bias current may also decrease the heat generation of the circuit and when the bias current is decreased by 30%, the consumed power is decreased by 30%.

There is a following method as another method of decreasing the power at the time of the fallback operation.

(a) Transmission energy to be applied is decreased by narrowing a transmission beam width. A driving pattern for each element of the ultrasonic transducer 203 is changed to narrow the beam width and total energy is decreased by decreasing a wave height value or decreasing a driving pulse width.

(b) Energy consumption per hour is decreased by prolonging an interval of repeated scanning. As a specific method of prolonging the interval of the repeated scanning, there are a method of prolonging a pulse repeating period and intermittent transmission to scan at a general short time interval during one heartbeat and provide a break period between each scanning.

(c) Activation of an operation mode in which the power consumption is large is inhibited, or selection of an operation parameter in which the power consumption becomes large is inhibited. For example, parameter selection such as to set a transmission focus in the distance, to set a transmission frequency to a high frequency, or to set a blood flow detection range by prolonging a driving wave length is inhibited.

(d) The number of operating elements of the ultrasonic transducer 203 used for transmission and reception is decreased to cut the power.

Also, since each of the above-described methods has an effect of cutting the power and there are a variety of levels of performance deterioration, the fallback operation is performed by appropriately combining them.

Figure 7:
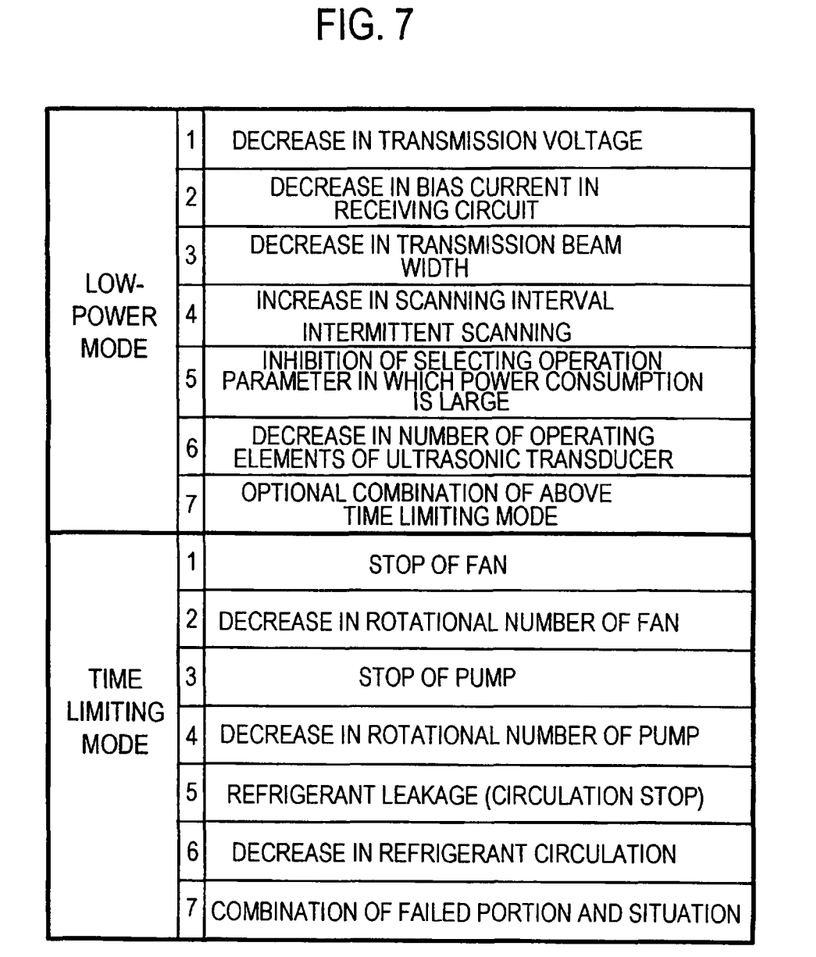
FIG. 7 is a view of a type of a fallback operation mode of an ultrasonic diagnostic device according to one embodiment.

Therefore, as illustrated in FIG. 7, a type of the low-power mode is set by changing the transmission condition by (1) decrease in the transmission voltage, (2) decrease in the bias current of the receiving circuit, (3) decrease in the transmission beam width, (4) increase in scanning interval or the intermittent scanning, (5) inhibition of selecting the operation parameter in which the power consumption is large, (6) decrease in the number of the operating elements of the ultrasonic transducer 203 used for transmitting and receiving, and (7) appropriate combination of the above-described conditions.

Also, for example, the time limiting mode in which maximum operating time is determined is set in accordance with cooling system abnormality determined by (1) stop of the fan 212, (2) decrease in rotating speed of the fan 212, (3) stop of the pump 210, (4) decrease in rotating speed of the pump 210, (5) stop of the circulation by the leakage of the refrigerant, (6) decrease in the refrigerant circulation, and (7) appropriate optional combination in accordance with a failure condition.

Also, the operating time is determined by considering current abnormality of a Peltier element in a case where the ultrasonic transducer 203 is cooled by the Peltier element and the like, and a state of the failed portion of another used cooling system in a case where a compressor is used in place of the pump 210.

Since each fallback operation mode has an effect of cutting the power and there are a variety of levels of the performance deterioration, it is preferable to perform the fallback operation by appropriately combining them depending on the situation.

First, when an operator selects a corresponding probe, detection of the temperature of the surface of the transducer from an output of the temperature detecting unit 209 is started (S301). Then, just after starting to detect, it is confirmed whether the temperature is an abnormal temperature, that is to say, whether this is higher than a predetermined temperature (S302). If there is temperature abnormality at this point of time before starting to drive, it is considered that there is abnormality in the temperature detecting unit and the operation cannot be continued, so that an operation stopping process is performed (S303).

Meanwhile, the temperature abnormality means in general the temperature higher than the predetermined temperature, and this may be detected by a comparing circuit for comparing the detected temperature with the predetermined temperature.

If the temperature is normal, next, abnormality detection of the cooling system is started (S304). In a case where the abnormality is detected at a step of judging the abnormality of the cooling system (S305), it is displayed on the display 19 that there is the abnormality in a cooling unit (S306).

The abnormality of the cooling system is detected by stop of rotation or decrease in rotating speed of the cooling fan, stop of rotation or decrease in rotating speed of a motor of a cooling pump, and stop of the circulation of the refrigerant or decrease in the circulation, for example.

As illustrated in FIG. 4, it is displayed on the display 19 where the abnormality is (S401). Next, a selection screen of the fallback operation is displayed (S307) to allow a user to select whether to stop the operation or continue the measurement by the fallback operation (S308). In an example of the menu illustrated in FIG. 4, one of (1) stopping the operation and stopping using, (2) continuously using in the low-power mode in which the diagnostic performance is sacrificed but the long time usage is possible, and (3) continuing to operate in full power by limiting the time, is selected (S402).

Also, it may be considered that the menu of the fallback operation selected in accordance with a failed state is further added, and it is possible to add a safety priority mode in which selection of an operation mode in which the power consumption is large and the transmission reception condition in which the power consumption is large is inhibited for improving safety, for example.

In a case where (1) is selected at the step S402 in FIG. 4, the operation is stopped (S309) (S403). In a case where (2) is selected, there is deterioration in the diagnostic performance such as deterioration in resolution of the image, so that a warning is displayed on the display 19 to gain approval of the user so as to avoid bad diagnosis (S404). Thereafter, the fallback operation mode in which the transmission voltage is decreased or the received bias current is decreased is performed, for example (S405).

In a case where (3) is selected, the operation in full power is performed by limiting the time in accordance with the failed portion (S406). In this case, even within displayed time, the operation is performed by giving first priority to the temperature detected by the temperature detecting unit and in a case where the temperature becomes higher than a reference temperature, the operation is stopped at that point of time.

Figure 5:
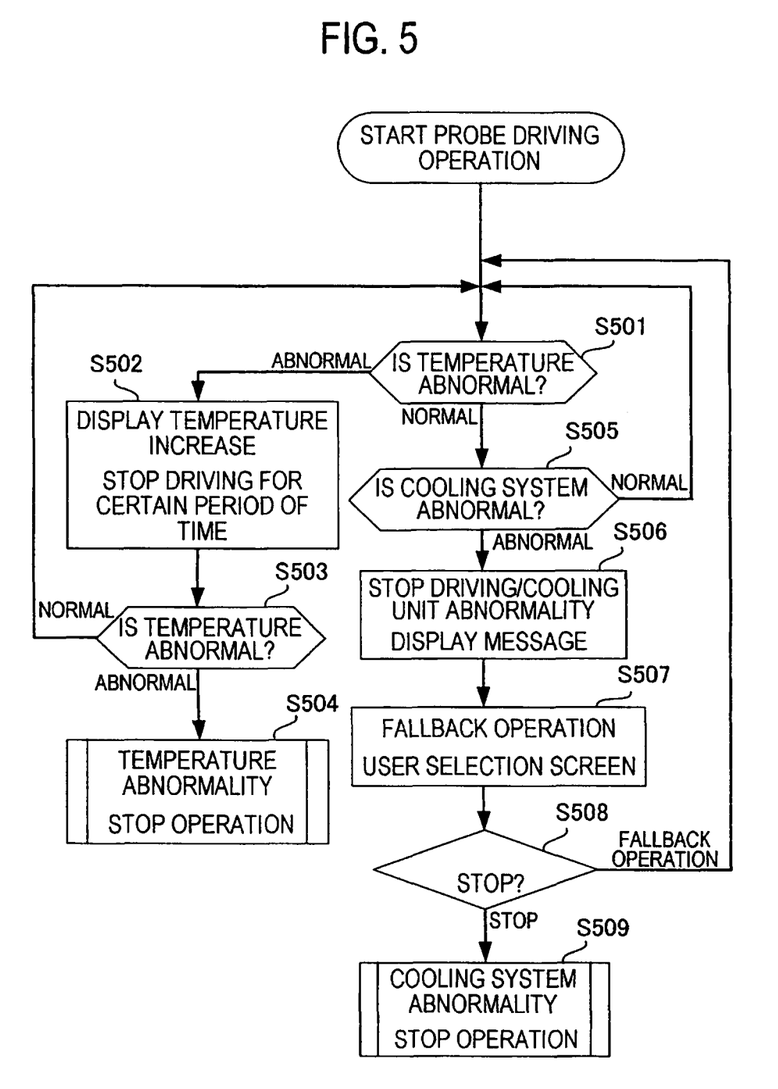
FIG. 5 is a flowchart of operation during measurement of the ultrasonic diagnostic device according to the first embodiment.

FIG. 5 is a flowchart illustrating operation during measurement of the ultrasonic diagnostic device according to the first embodiment. When there is no abnormality in the initial operation illustrated in FIG. 3, driving of the corresponding probe is started. In a using state also, the temperature abnormality and the cooling system abnormality are continuously monitored.

In a case where the temperature abnormality is detected at a step S501, the increase in temperature is displayed on the display 19 and the transmission is stopped for a certain period of time to wait for cooling (S502). In a case where the temperature does not decrease after a certain period of time at a step S503, it is judged to be abnormal and the operation is stopped (S504). In a case where the temperature decreases, the driving is started again and the procedure returns to the step S501.

In a case where the abnormality in the cooling system is first detected during the measurement at a step S505, the driving is stopped and the abnormality in the cooling unit is displayed on the display 19 (S506). The selection screen of the fallback operation illustrated in FIG. 4 is displayed and the operator is prompted to select the fallback operation (S507).

It is desirable that a type of the fallback operation selection is changed in accordance with a mode of the failure, that is to say, a state of the cooling abnormality. For example, in a case where the abnormality is detected in all the cooling systems, there is a case in which the fallback operation is dangerous. It is also possible to configure such that only the driving stop may be selected in such a case.

It is also considered to prepare a plurality of low-power modes. In a case where there is the abnormality only in the fan 212, since the heat is transmitted to the connecter unit 11 through the cable 12, cooling to a certain extent may be expected. By supplying much more power than that in a case where the circulation of the refrigerant is stopped by detecting the abnormality by the cooling circulation monitoring unit 214 to the ultrasonic probe unit 13 also, the surface temperature of the ultrasonic probe unit 13 may be controlled to be within an allowable range.

In a case where it is selected to stop at a step S508, the operation is stopped (S509). In a case where the fallback operation is selected, the procedure returns to the step S501 and the fallback operation is continued while whether the temperature abnormality and further another cooling system abnormality do not occur is monitored.

By the above-described configuration, the operator may confirm presence or absence of the failure of the ultrasonic probe unit by the display when selecting the probe and when using the same prove and may select safe fallback operation in accordance with a degree of the failure in a case where there is the failure. In accordance with this, the diagnosis may be continued.

Figure 6:
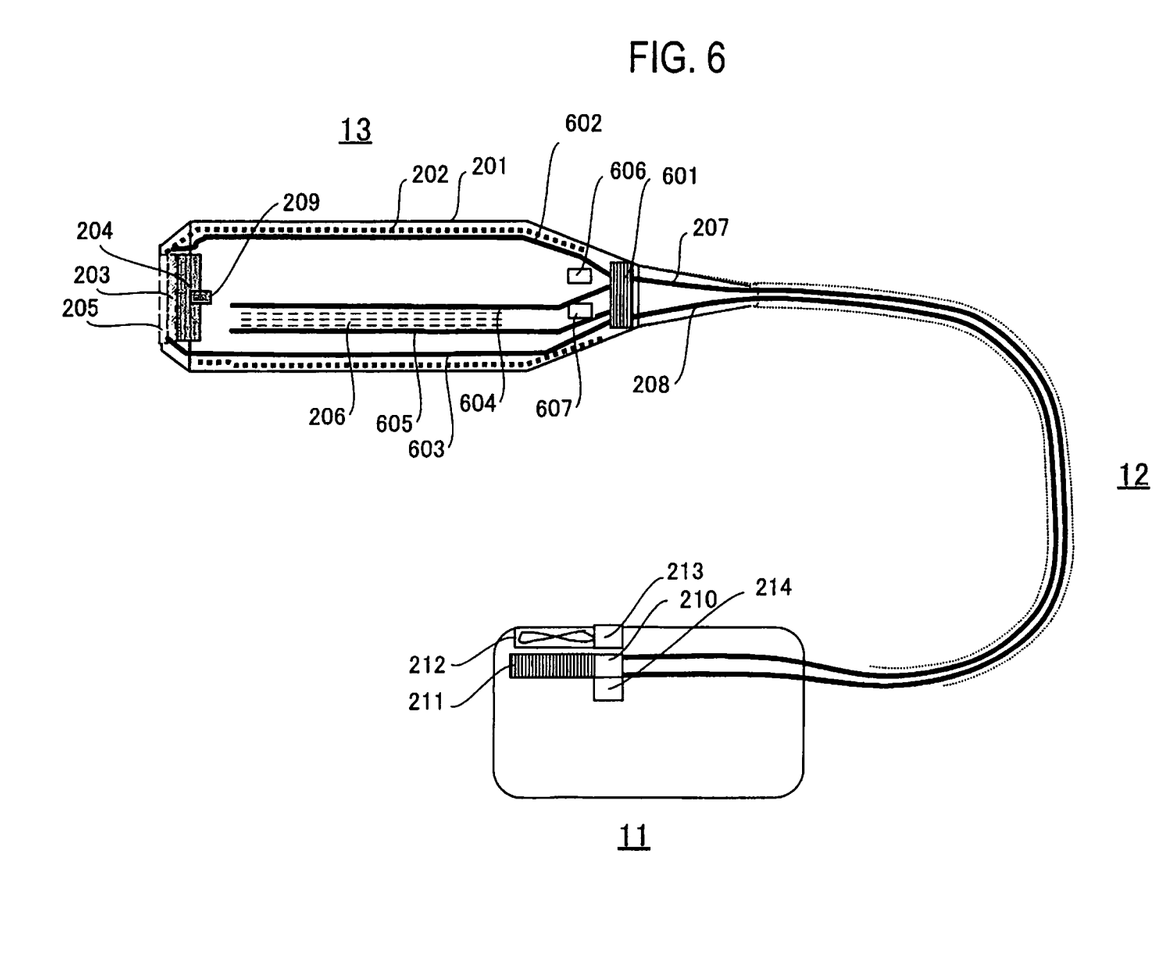
FIG. 6 is a configuration example of a probe of an ultrasonic diagnostic device according to a second embodiment.

FIG. 6 is a configuration example of the probe of the ultrasonic diagnostic device according to a second embodiment. This is identical to that in the first embodiment illustrated in FIG. 3 in that the cooling is performed by the connector unit 11 and the refrigerant circulates in the cable 12, in this embodiment, a heat exchanger 601 is provided within a probe grip (probe unit exterior) 201 of the ultrasonic probe unit 13 and the refrigerant, which circulates in the cable, is not directly sent to the shielding material 202 or the electronic circuit board 206 and is used once for cooling the heat exchanger 601.

A low-temperature transducer cooling system 602 and a high-temperature transducer cooling system 603 for cooling the ultrasonic transducer 203 are connected to the heat exchanger 601 to transmit the heat of the ultrasonic transducer 203 to the heat exchanger 601. Also, it is configured such that the heat of the electronic circuit board 206 is also transmitted to the heat exchanger 601 by a low-temperature circuit cooling system 604 and a high-temperature circuit cooling system 605.

As the abnormality detection of the cooling system in this embodiment, there are transducer cooling system abnormality detecting unit 606 and circuit cooling system abnormality detecting unit 607 in addition to the rotation monitoring unit 213 of the fan and the cooling circulation monitoring unit 214 for detecting the abnormal operation of the pump and the leakage of the refrigerant in FIG. 2, and presence or absence of the abnormality of each cooling system is detected. By performing subdivided failure detection, it becomes possible to correctly comprehend a degree of the failure/defect state in more detail and select safe and optimal fallback operation.

By adopting the configuration to separate the cooling system in this manner, by separating the circulation system in the probe cable 12 in which possibility of the failure is the highest and the cooling system in the probe handle 201 (cooling system of the ultrasonic transducer 203 and the electronic circuit board 206), the cooling system in the probe handle 201 continuously operates even when there is the leakage of the refrigerant in the cable and it is possible to cool the ultrasonic transducer 203 and the electronic circuit board 206 by the refrigerant as compared to the case of the failure in the single cooling system described in the first embodiment.

Also, although the temperature of the ultrasonic transducer 203 is required to be controlled to 40° C. or lower, for example, it is sufficient to control the temperature of the electronic circuit board 206 to a relatively high temperature (for example, approximately 80° C.). Cooling efficiency may be improved using difference in cooling target temperature. In a case where the ultrasonic transducer 203 is directly cooled by the Peltier element and the like, the temperature of the high-temperature transducer cooling system 603 increases due to the heat generated from the Peltier element. In such a case also, there is still the temperature difference with the high-temperature circuit cooling system, so that it is possible to connect them to the same heat exchanger 601.

Meanwhile, although the pump is used as refrigerant circulating means in the probe cable 12 in the embodiment of the invention, a small compressor may also be used.

Also, since flexibility is not especially required in the transmission of the heat in the probe handle 201, a copper plate, a copper foil, a heat pipe, the small compressor and a material utilizing a heat emission property may also be used in addition to the above-described refrigerant circulating method.

Further, the cooling of the heat radiator of the connector unit 11 may be performed by direct transmission of the heat to the heat exchanger arranged in the ultrasonic diagnostic device main body 10 in addition to the fan.

Although an example of the probe unit having the electronic circuit board embedded therein is described in this embodiment, it goes without saying that this may be applied also to the heat radiation of the transducer in the probe unit without the electronic circuit board embedded therein.

In the above-described embodiment, the temperature of the ultrasonic transducer is detected before the abnormality of the cooling system (cooling mechanism) is detected, and in a case where the detected temperature is higher than the predetermined temperature, the operation for the diagnosis by the ultrasonic probe is stopped. However, in a case in which it is checked in advance and the like, the temperature detection of the ultrasonic transducer may be omitted.

As described above, in the ultrasonic diagnostic device according to the embodiment, there is an effect that, even when there is the failure in the cooling system, this may be continuously used by the fallback operation in accordance with the situation. Further, the detailed fallback operation corresponding to the degree of the failure is possible and the safe fallback operation may be realized.

Also, the invention is not limited to the above-described embodiment as it is and may be embodied by changing the components within a scope without departing from the spirit thereof in a practical phase. Various inventions may be formed by appropriately combining a plurality of components disclosed in the above-described embodiment. For example, some of the components may be deleted from all the components described in the embodiment. Further, the components in the different embodiments may be appropriately combined. The variations are also included in the invention as far as the technical idea of the invention is used.

REFERENCE SIGNS LIST

10 ultrasonic diagnostic device main body
11 connector unit
12 probe cable
13 ultrasonic probe unit
201 probe unit exterior (probe handle)
202 shielding material
203 ultrasonic transducer
204 backing material
205 lens material
206 electronic circuit board
207 low-temperature cooling system
208 high-temperature cooling system
209 temperature detecting unit
210 pump
211, 601 heat exchanger
212 fan
213 fan rotation monitoring unit
214 cooling circulation monitoring unit
602 low-temperature transducer cooling system
603 high-temperature transducer cooling system
604 low-temperature circuit cooling system
605 high-temperature circuit cooling system
606 transducer cooling system abnormality detecting unit
607 circuit cooling system abnormality detecting unit

The invention claimed is:

1. An ultrasonic diagnostic device, comprising:
    a cooling mechanism configured to cool an ultrasonic probe unit by circulating a refrigerant in a cable of the ultrasonic probe unit in which ultrasonic transducers are provided;
    a cooling abnormality detecting unit configured to detect an abnormal state in the cooling mechanism; and
    an operating unit configured to, when the abnormal state of the cooling mechanism is detected by the cooling abnormality detecting unit, perform a fallback operation to change a transmission reception condition of the ultrasonic transducers in accordance with the detected abnormal state,
    wherein a list of fallback operations with respect to the abnormal state is displayed on a display screen for selection by an operator.

2. The ultrasonic diagnostic device of claim 1, wherein the abnormal state is a decrease in rotation or a stopping of a cooling fan in a connector unit of the ultrasonic probe unit.

3. The ultrasonic diagnostic device of claim 1, wherein the fallback operations include limiting continuous use time.

4. The ultrasonic diagnostic device of claim 1, wherein the fallback operations include a change in the transmission reception condition, which is a change that includes a decrease in transmission beam width.

5. The ultrasonic diagnostic device of claim 1, wherein the fallback operations include a change in the transmission reception condition, which is a change that includes intermittent scanning or an increase in a scanning interval.

6. The ultrasonic diagnostic device of claim 1, wherein the fallback operations include inhibiting an operation mode or selection of a transmission reception condition in which power consumption is large.

7. The ultrasonic diagnostic device of claim 1, wherein the fallback operations include a change in the transmission reception condition, which is a change that includes a decrease in a number of operating elements of the ultrasonic transducers.

* * * * *